(12) United States Patent
Murakami et al.

(10) Patent No.: US 7,796,013 B2
(45) Date of Patent: Sep. 14, 2010

(54) DEVICE USING HISTOLOGICAL AND PHYSIOLOGICAL BIOMETRIC MARKER FOR AUTHENTICATION AND ACTIVATION

(75) Inventors: Rick V. Murakami, North Ogden, UT (US); David Miller, Morgan, UT (US); Matthew W. Pettit, Mountain Green, UT (US)

(73) Assignee: Ensign Holdings, Salt Lake City, UT (US)

( * ) Notice: Subject to any disclaimer, the term of this patent is extended or adjusted under 35 U.S.C. 154(b) by 2011 days.

(21) Appl. No.: 09/758,836

(22) Filed: Jan. 10, 2001

(65) Prior Publication Data

US 2007/0063816 A1    Mar. 22, 2007

Related U.S. Application Data

(60) Provisional application No. 60/175,460, filed on Jan. 10, 2000.

(51) Int. Cl.
*G05B 19/00* (2006.01)
*G06F 7/04* (2006.01)
*G08B 29/00* (2006.01)
*H04B 1/00* (2006.01)
*H04Q 1/00* (2006.01)

(52) U.S. Cl. ............. 340/5.82; 340/5.52; 340/5.53; 455/411; 382/124; 382/115

(58) Field of Classification Search ......... 340/5.8–5.84, 340/5.52–5.53; 382/124, 115; 235/380, 235/492, 379, 381; 455/411; 600/310, 316–317, 600/322
See application file for complete search history.

(56) References Cited

U.S. PATENT DOCUMENTS

| | | | |
|---|---|---|---|
| 4,109,237 A | 8/1978 | Hill | 340/146.3 |
| 4,537,484 A | 8/1985 | Fowler et al. | |
| 4,544,267 A | 10/1985 | Schiller | |
| 4,582,985 A * | 4/1986 | Lofberg | 235/380 |
| 4,614,861 A * | 9/1986 | Pavlov et al. | 235/380 |
| 4,699,149 A | 10/1987 | Rice | |
| 4,728,186 A | 3/1988 | Eguchi et al. | |

(Continued)

FOREIGN PATENT DOCUMENTS

EP    1 916 615 A1    4/2008

(Continued)

OTHER PUBLICATIONS

Office Action for U.S. Appl. No. 09/815,885, filed Mar. 23, 2001, mailed from USPTO on Mar. 17, 2008, 12 pgs.

(Continued)

*Primary Examiner*—Brian A Zimmerman
*Assistant Examiner*—Nam V Nguyen
(74) *Attorney, Agent, or Firm*—John R. Thompson; Stoel Rives LLP (57) ABSTRACT

A biometrically activated device wherein data derived from detection of unique internal biometric traits are stored within said biometrically activated device to be compared to stored data relative to said internal biometric markers or traits previously scanned from a user of said biometrically activated device. The biometrically activated device may allow or disallow access to information, or provide use of, data or a device protected by the biometrically activated device.

35 Claims, 3 Drawing Sheets

U.S. PATENT DOCUMENTS

| | | | |
|---|---|---|---|
| 4,784,484 A | | 11/1988 | Jensen |
| 5,073,950 A | | 12/1991 | Colbert et al. |
| 5,077,803 A | | 12/1991 | Kato et al. |
| 5,088,817 A | | 2/1992 | Igaki et al. |
| 5,103,486 A | | 4/1992 | Grippi |
| 5,172,698 A | | 12/1992 | Stanko ........................ 128/697 |
| 5,180,901 A | * | 1/1993 | Hiramatsu ................... 235/380 |
| 5,230,025 A | | 7/1993 | Fishbine et al. |
| 5,335,288 A | | 8/1994 | Faulkner |
| 5,456,256 A | * | 10/1995 | Schneider et al. ............ 600/445 |
| 5,482,034 A | * | 1/1996 | Lewis et al. .................. 600/323 |
| 5,526,808 A | | 6/1996 | Kaminsky |
| 5,586,171 A | | 12/1996 | McAllister et al. ............. 379/67 |
| 5,623,552 A | * | 4/1997 | Lane ........................... 382/124 |
| 5,666,400 A | | 9/1997 | McAllister et al. |
| 5,704,352 A | | 1/1998 | Tremblay et al. ............ 128/630 |
| 5,719,950 A | | 2/1998 | Osten et al. |
| 5,737,439 A | | 4/1998 | Lapsley et al. |
| 5,774,571 A | | 6/1998 | Marshall |
| 5,787,185 A | * | 7/1998 | Clayden ..................... 382/115 |
| 5,789,733 A | | 8/1998 | Jachimowicz et al. ........ 235/492 |
| 5,872,834 A | | 2/1999 | Teitelbaum .............. 379/93.03 |
| 5,935,062 A | * | 8/1999 | Messerschmidt et al. .... 600/322 |
| 5,974,337 A | * | 10/1999 | Kaffka et al. ................ 600/316 |
| 5,982,914 A | * | 11/1999 | Lee et al. ..................... 382/124 |
| 5,987,232 A | | 11/1999 | Tabuki |
| 6,088,585 A | * | 7/2000 | Schmitt et al. ............... 455/411 |
| 6,104,913 A | | 8/2000 | McAllister |
| 6,104,922 A | | 8/2000 | Baumann |
| 6,148,094 A | | 11/2000 | Kinsella |
| 6,164,403 A | | 12/2000 | Wuidart |
| 6,171,112 B1 | | 1/2001 | Clark et al. |
| 6,182,892 B1 | | 2/2001 | Angelo et al. |
| 6,193,153 B1 | | 2/2001 | Lambert |
| 6,202,151 B1 | | 3/2001 | Musgrave et al. |
| 6,208,264 B1 | | 3/2001 | Bradney et al. |
| 6,219,639 B1 | | 4/2001 | Bakis et al. |
| 6,225,890 B1 | | 5/2001 | Murphy |
| 6,232,874 B1 | | 5/2001 | Murphy |
| 6,266,566 B1 | | 7/2001 | Nichols et al. |
| 6,269,348 B1 | | 7/2001 | Pare, Jr. et al. |
| 6,275,806 B1 | | 8/2001 | Pertrushin |
| 6,289,453 B1 | | 9/2001 | Walker et al. |
| 6,483,929 B1 | | 11/2002 | Murakami et al. |
| 6,496,595 B1 | | 12/2002 | Puchek et al. |
| 6,628,809 B1 | * | 9/2003 | Rowe et al. .................. 382/115 |
| 6,681,029 B1 | | 1/2004 | Rhoads |
| 6,816,605 B2 | | 11/2004 | Rowe et al. |
| 6,898,299 B1 | * | 5/2005 | Brooks ....................... 382/115 |
| 6,920,231 B1 | | 7/2005 | Griffin |
| 7,113,616 B2 | | 9/2006 | Ito et al. |
| 7,133,792 B2 | | 11/2006 | Murakami et al. |
| 7,188,362 B2 | | 3/2007 | Brandys |
| 7,214,953 B2 | | 5/2007 | Setlak et al. |
| 7,358,514 B2 | | 4/2008 | Setlak et al. |
| 7,441,123 B2 | | 10/2008 | Grant et al. |
| 2001/0033220 A1 | | 10/2001 | Stone et al. ................. 340/5.52 |
| 2002/0138768 A1 | | 9/2002 | Murakami et al. |
| 2002/0174347 A1 | | 11/2002 | Ting |
| 2003/0128867 A1 | | 7/2003 | Bennett |
| 2003/0233557 A1 | | 12/2003 | Zimmerman |
| 2004/0187037 A1 | | 9/2004 | Checco |
| 2005/0223234 A1 | | 10/2005 | McOwen et al. |
| 2005/0267752 A1 | | 12/2005 | Navratil et al. |
| 2006/0067573 A1 | | 3/2006 | Parr et al. |
| 2006/0093190 A1 | | 5/2006 | Cheng et al. |
| 2006/0116970 A1 | | 6/2006 | Scherzer et al. |
| 2006/0171571 A1 | | 8/2006 | Chan et al. |
| 2006/0210119 A1 | | 9/2006 | Willis et al. |
| 2006/0293892 A1 | | 12/2006 | Pathuel |
| 2007/0016088 A1 | | 1/2007 | Grant et al. |
| 2007/0016777 A1 | | 1/2007 | Henderson et al. |
| 2007/0063816 A1 | | 3/2007 | Murakami et al. |
| 2007/0129941 A1 | | 6/2007 | Taveres |
| 2007/0192591 A1 | | 8/2007 | Yumoto et al. |
| 2008/0242231 A1 | | 10/2008 | Gray |
| 2008/0260211 A1 | | 10/2008 | Bennett et al. |

FOREIGN PATENT DOCUMENTS

| | | |
|---|---|---|
| JP | SHO 60-126787 | 7/1985 |
| JP | SHO 61-175865 | 8/1986 |
| JP | SHO 63-20583 | 1/1988 |
| JP | SHO 63-53099 | 3/1988 |
| JP | SHO 63-120385 | 5/1988 |
| JP | SHO 63-313288 | 12/1988 |
| JP | HEI 1-175362 | 12/1989 |
| JP | HEI 4-24889 | 1/1992 |
| JP | 2000-181871 | 6/2000 |
| WO | WO 88/04153 | 6/1988 |
| WO | WO 98/37519 | 8/1998 |

OTHER PUBLICATIONS

Biel, Lena et al., "ECG Analysis: A New Approach in Human Identification," 1999 IEEE, pp. 557-561.

Office Action for U.S. Appl. No. 10/300,659, filed Nov. 19, 2002, mailed from the USPTO on Dec. 27, 2007, 15 pgs.

Office Action for U.S. Appl. No. 09/814,607, filed Mar. 22, 2001, mailed from the USPTO on Dec. 19, 2008, 14 pgs.

International Search Report for PCT/US09/31638, filed Jan. 22, 2009, mailed Mar. 6, 2009, 12 pgs.

Kachigan, Sam Kash, "Multivariate Statistical Analysis," Radius Press, 1991, 1986, 1982, 4 pgs.

Hayes, Matthew J., et al., "Quantitative Evaluation of Photoplethysmographic Artefact Reduction for Pulse Oximetry," Optical Engineering Group, Department of Electrical and Electronic Engineering, Loughborough University, Loughborough, Leicestershire, LE11 3TU, UK, SPIE vol. 3570, Sep. 1, 1998, 14 pgs.

Scholz, Udo, J., "Multivariate Spectral Analysis of the Beat-to-Beat Sampled Cortical NIRS-Signals and the Heart Rate Variability," Department of Neurology, Charite, Humboldt University, Berlin, Germany, SPIE vol. 3566, Sep. 1998, 6 pgs.

Hoeksel, S.A., et al., "Detection of Dicrotic Notch in Arterial Pressure Signals," Department of Anesthesiology, Cardiovascular Research Institute Maastricht, Maastricht University, The Netherlands, www.medscape.com, 1997, 1 pg.

Cysewska-Sobusiak, Anna, "Noninvasive Monitoring of Arterial Blood Oxygenation with Spectrophotometric Technique," Institute of Electronics and Communications, Technical University of Poznan, Piotrowo 3a, PL-60-965 Poznan, Poland, SPIE vol. 1711, 1992, 14 pgs.

"Artificial Pacemaker," Wikipedia, the free encyclopedia, 3 pgs.

"Type: Rate-Responsive Pacing Systems," Medtronic, 1 pg.

Leichter, I., et al., "Effect of Age and Sex on Bone Density, Bone Mineral Content and Cortical Index," Energy Citations Database (ECD)—Energy and Energy-Related Bibliographic Citations, May 1, 1981, 2 pgs.

Miller, Paul D., M.D., "Increased Age Is a Risk Factor," "Assessing Fracture Risk: Which Factors Are Clinically Most Important?" 4 pgs.

Smith, SL, "Attribution of Hand Bones to Sex and Population Groups," Journal of Forensic Sciences, vol. 41, Issue 3, www.astm.org/cgi-bin/SoftCart.exe/JOURNALS/FORENSIC/PAGES/JFS41396046, May 1996, printed Jan. 14, 2007, 1 pg.

Jain, Anil K., et al., "Multibiometric Systems," Communications of the ACM, Jan. 2004, vol. 47, No. 1, pp. 34-40.

* cited by examiner

DEVICE USING HISTOLOGICAL AND PHYSIOLOGICAL BIOMETRIC MARKER FOR AUTHENTICATION AND ACTIVATION

RELATED APPLICATIONS

This application claims priority to provisional patent application 60/175,460, filed Jan. 10, 2000.

BACKGROUND OF THE INVENTION

1. Field of the Invention

The present invention relates generally to a biometrically activated device. More specifically, the invention relates to a biometrically activated device capable of authenticating or verifying a user's identity based on a unique internal biometric marker, or combination of unique internal biometric markers, of a user, thereby allowing or denying access to and/or control over an electronic component.

2. State of the Art

Security devices have been around for ages. From drawbridges to locks on doors and furniture, people have attempted to secure their well-being and personal belongings from harms way. As technological advances were made, new means of security were created. Door locks require codes to disengage the lock, car doors are equipped with number pads, vehicle ignition keys include microchips encoded to communicate with the vehicle so as to prevent theft. Financial transactions have also become more secure. Currency is more sophisticated in order to thwart copying, credit cards require authentication signatures, bank account access requires account numbers, and personal identification numbers are issued for everything from calling cards to internet access to stock market trading accounts.

As technology continues to advance at a rapid rate, the search for more sophisticated, unbreakable, security measures continues. The key to an effective security system is the identification of the individual or entity attempting to access that which is protected by the security system, be it a home, financial information, or communications. Mechanical keys can be copied, personal identification numbers stolen, and credit cards misused without much trouble. The level of theft is evident from the billions of dollars in fraudulent financial transactions taking place each year, stolen vehicles, and home break-ins. Of particular concern is the relatively new crime wherein a persons 'identity' is stolen. In this day and age, a person's identity is closely tied to a bank account number, a phone number, an identification number, a social security number, or other such information which is easily stolen and then used to access the owner's information or property. When such a crime occurs, the victim suffers financial decimation, credit destruction, and countless hours of agony in attempting to 'rebuild' their 'identity'.

One form of fraud involves electronic transaction fraud, such as fraudulent credit and debit card transactions. Typically, a magnetic strip on one surface of such cards carries an electronic form of a series of numbers, which identifies the account to be credited or debited. To execute a financial transaction using such a card, all that is needed is the series of numbers and authentication that the card is being used by the authorized user. Such authorization typically consists of photo identification or verification of a signature if the card is being used in a person to person transaction. Transactions conducted through other media, such as the telephone or over the internet, are often authenticated using some other form of identification, such as the billing address or phone number of the authorized user of the card. Because this information is often readily available to the public, such authentication processes are not very secure.

In the electronic transaction market, efficient identification of people is not only very critical, but very difficult, due to the rapid nature of monetary exchanges. In cases of pure electronic transactions, there is no physical document that acts as a transaction mechanism. In addition to this, most electronic transactions are performed from a location that is remote relative to the funds involved. The identification of the holder of the transaction device, such as a credit card, is the responsibility of the merchant or third party willing to accept an electronic transaction. Accurate identification and authentication of the validity of the transaction device is not always possible and, even when obtained, is not always accurate.

The advent of the internet has added an entirely new dimension to the problems associated with electronic transaction fraud. The internet provides a medium wherein the user of a transaction device and a third party willing to accept an electronic transfer of funds never have any actual contact. This creates further authentication problems for the third party because the transfer device is not physically present, the identification of the user is not visually apparent, and a telephone number cannot be authenticated. As a result of the increased use of e-commerce, and ensuing authentication difficulties therewith, the incidence of electronic transaction fraud has been on the increase. In the immediate future, the opportunity and incidence of fraud will increase correspondingly unless sufficient security measures capable of positively identifying an individual are implemented.

The market has responded to the difficulties of authenticating electronic transfer devices, and positively identifying individuals, by searching for a viable biometric solution to the problems. Biometric technology generally involves the electronic identification of an individual using physiological traits which are unique to that same individual. Fingerprints are an excellent example of a biometric marker used for years to provide the unique identification of individuals. Because a fingerprint is unique to an individual, the identity of that individual may be determined through an analysis of the fingerprint. Thus, the identity of the individual, determined from a fingerprint, may act as a 'key' to unlock data or allow access through a door.

In particular, fingerprints have been used to secure some transactions and have been proposed for use in other areas. Many banks require that a finger print or thumb print of a person cashing a check be placed on the check. This allows the bank to later verify or identify anyone passing fraudulent checks. Along a similar line, it has been proposed that Automated Teller Machines (ATM) be equipped with fingerprint pads to provide further security to ATM transactions. An ATM having a fingerprint pad would require the user to validate their ATM card byway of their fingerprint. This could be accomplished by inserting the ATM card into the machine, entering a Personal Identification Number (PIN), and then requiring the user to place their thumb or finger on the pad so that the ATM machine can analyze the fingerprint and confirm the identity of the individual using the card. Such a system would necessarily rely on a database built into the ATM or connected to the ATM, to provide a list of users and corresponding fingerprint information. The fingerprint of the user could be compared to the data in the database to confirm that the ATM card being used did in fact belong to the person associated with the fingerprint placed on the fingerprint pad of the ATM.

Other known biometric markers include palm prints, iris scans, proportional comparison of physical traits, and voice recognition. For the most part, these biometric markers, like the fingerprint, are external physiological traits or characteristics. Information unique to an individual is gathered through various scanning processes which scan a external biometric marker of an individual. A number of United States Patents discuss biometric devices which may be used to help identify a person. Examples of external biometric devices include those described in U.S. Pat. Nos. 4,537,484; 4,544,267; 4,699,149; 4,728,186; 4,784,484; 5,073,950; 5,077,803; 5,088,817; 5,103,486; 5,230,025; and 5,335,288 Internal biometric data has also been used to verify that a subject is alive. Such verifications have been accomplished by passively verifying physiological process, such as registering electrical impulses (EKG), or actively verifying physiological norms by introducing and capturing a modified signal, such as introducing light energy to determine blood gas content (pulse oximeter). Examples of such biometric readings are describe in U.S. Pat. Nos. 5,719,950; and 5,737,439. The disclosures of each of the patents listed above are hereby incorporated by reference.

One of the downfalls of using the devices which are currently available in the market for analyzing external biometric markers is the cost of installing the necessary scanning devices to provide the required security. For each different trait to be tested, whether it is a fingerprint, retinal scan, voice print, or the like, a different piece of expensive scanning equipment is necessary. Installation of such equipment into machines such as ATMs is economically impractical because each ATM would require the installation of the expensive scanning device.

Another downfall of the biometric scanning devices currently available is their size. The necessary scanning equipment is bulky, making it impractical to attach the scanning equipment to portable devices such as cell phones, credit cards, personal data assistants, portable computers, and the like.

Further, incompatibility across multiple systems renders the deployment of standard biometric identification on a wide scale very challenging, if not impossible. In addition, large databases storing the vast amount of data necessary to authenticate biometrically activated transactions or authentications result in further costs which have heretofore made biometric identification a poor candidate as a security device for low level or mass produced systems.

The downfalls of the current biometrically activated security systems can be overcome through the use of portable biometrically activated devices which only store the biometric profile of a single individual or a small group of individuals. The use of unique internal biometric markers, rather than external biometric markers, provides advantages which overcome the downfalls of the present biometric scanning devices used for security and the identification of individuals.

BRIEF SUMMARY OF THE INVENTION

The present invention provides an apparatus and process which utilizes unique internal human biometric markers to verify the identity of the user of the biometrically activated device or provide access or control over an electronic component. More specifically, the biometrically activated device of the present invention allows non-invasive access to a unique internal biometric marker, or some combination of unique internal biometric markers, and compares the scanned biometric marker to a biometric marker or profile stored within the biometrically activated device, thereby attempting to verify the identity of an individual using the biometrically activated device. A biometric marker, for the purposes of this invention, is a human internal physiological characteristic, or biologically active feature, which, preferably, is unique to each individual member of the human race. The biometric markers of the present invention are not merely measurements of superficial anatomical structure, but instead utilize or alternatively include measurements of physiological traits of the various systems of the human body and/or are histological traits associated with tissues of the human body. In addition, a unique biometric marker is one which does not significantly vary over time such that the biometric marker is always unique to the individual. The device scans a selected body part or biological feature of the user, taking an internal biometric measurement or recording internal biometric data from the same.

A biometric profile of the subject attempting to activate the biometrically activated device may be electronically constructed from the data or measurement obtained. The profile, measurement, or data is then analyzed and compared to a stored biometric profile, or profiles, to determine whether or not the user is authorized to use the device or access the information that the biometrically activated device is protecting. As with a conventional door key, the authorization or verification of a valid user triggers the biometrically activated device to unlock certain information or activate or provide access to that which the device is protecting.

In its simplest form, the biometrically activated device comprises a biometric sensor and a memory module. The biometric sensor obtains the requisite internal biometric measurements or data from a user and compares the measurements or data to a biometric profile stored within the memory module. If the biometric profile stored in the memory module matches the measurements or data obtained from the user of the biometrically activated device, the biometrically activated device provides access to the data stored within a memory module, triggers the disengagement of a locking mechanism, or performs a function on a mechanical device.

The biometrically activated device transmits or emits energy towards a human user. A portion of the emitted energy is reflected back to the biometrically activated device where it is received. The received signal is then transformed into an electric signal which represents a unique biometric profile of the user. The profile may then be compared to a biometric profile stored in the memory module of the biometrically activated device. If the user's profile matches a profile stored within the memory module, the biometrically activated device is activated or is permitted to function in the manner in which it is programmed to function.

The biometrically activated device can provide a means to control access, secure information, initiate electrical components, or provide a general security system. The internal biometric marker or combination of markers scanned is unique to each individual and, thus, difficult or impossible to otherwise reproduce. Likewise, the biometric profile stored within a biometrically activated device is unique to the device. Without knowledge of the specific internal biometric marker or markers scanned by the biometrically activated device, a biometric profile cannot be reverse engineered or reconstructed so as to activate the biometrically activated device. In other words, the biometrically activated device may scan a user for numerous unique biometric markers, however, without knowing which marker is compared within the memory module, reverse engineering is virtually impossible. In this fashion, the biometrically activated device provides superior security features over present day security systems.

The biometrically activated device of the present invention focuses on internal biometric markers unique to a specific individual, instead of external biometric markers, such as fingerprints, or non-unique biometric markers, such as blood pulse readings, and overcomes the problems associated with traditional security systems to provide a more viable alternative to the external biometric sensors currently available.

BRIEF DESCRIPTION OF THE DRAWINGS

While the specification concludes with claims particularly pointing out and distinctly claiming that which is regarded as the present invention, the advantages of this invention can be more readily ascertained from the following description of the invention when read in conjunction with the accompanying drawings in which:

DESCRIPTION OF THE ILLUSTRATED EMBODIMENTS

Generally, the biometrically activated device of the present invention comprises a sensor for sensing or determining certain internal biometric markers of a user in communication with a memory module for storing biometric data or biometric profiles of a user or users corresponding to the internal biometric markers obtained by the sensor. When a user attempts to activate the biometrically activated device, the biometric sensor creates a biometric profile of the user and compares that profile with the stored biometric profile of an authorized user. If the user's profile does not match the profile of an authorized user, the data or information stored within the biometrically activated device is unretrievable. However, if the user's profile matches that of an authorized user, the biometrically activated device becomes activated for a set duration of time, thereby providing access to the data or information stored within the biometrically activated device or allowing the user to operate an apparatus which the biometrically activated device protects.

The biometric sensor is configured to determine specific unique internal biometric markers of a user. In a preferred embodiment of the invention, the sensor includes an emitter and a receiver. The emitter emits light or another form of energy which is partially absorbed and partially reflected by a portion of flesh of a user. Such light or energy may include, but is not limited to, ultrasonic energy, infra red light, near infra red light, ultra violet light, specific wavelength-visible or nonvisible light, white light, or electrical signals. The receiver collects those portions of light or energy that are reflected from the user. Based upon the light or energy reflected, data relating to internal biometric markers may be determined and a biometric profile of the user may be constructed. Some of the internal biometric markers which may be measured or determined from the biometric sensor include, but are not limited to, bone density, electromagnetic waves, cardiac rhythms, diacrotic notch readings, blood oxygen levels, capillary density, glucose levels, hematocrit levels, or sub-dermal layer analysis. Other biometric markers, such as bio-electric signals, resistance, impedance, capacitance, or other detectable electrical signals emanating from the body may also be detected by the sensor and used or combined with the feedback to the receiver to create a biometric profile of the user.

The biometric sensor may also include an activation device for activating the biometric sensor so that the biometric sensor is not always activated. Examples of the biometric sensor portion of the biometrically activated device of the present invention are more fully explained in the examples described below.

The memory module of the biometrically activated device is capable of receiving and storing data. The memory module is also capable of performing functions on the stored or received data to effectuate the creation of a biometric profile for a user. A biometric profile is based upon an internal biometric marker or markers of the user. Energy signals obtained from the biometric sensor may be converted into electrical signals which in turn may be converted to a biometric profile based upon a mathematical algorithm or transformation. The memory module may also store the commands or programming which will allow access to the apparatus being protected, or stored data such as phone numbers, account codes, or other information which a user wishes to keep private. Examples of the memory module of the present invention are further explained below.

Because the biometrically activated device is based upon a user's profile, the biometrically activated device is at least capable of accepting an initial biometric profile corresponding to the desired authorized user. The profile may be determined from the first use of the biometrically activated device or, alternatively, programmed before the first use in accordance with predefined biometric profiles.

Figure 1:
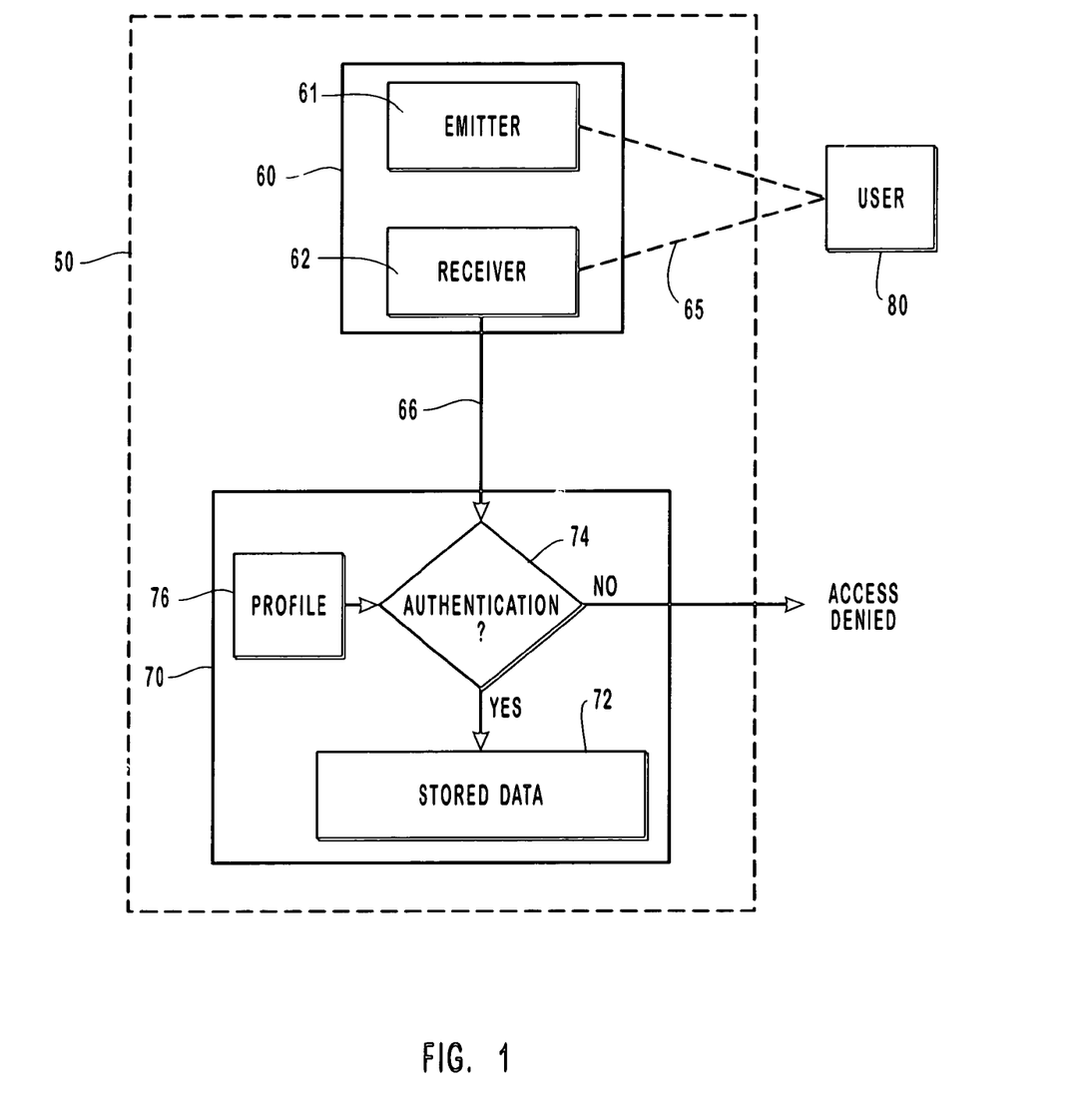
FIG. 1 is a schematic of a preferred embodiment of a biometrically activated device.

FIG. 1 illustrates a schematic of the preferred embodiment of the biometrically activated device of the present invention. The device 50 includes a biometric sensor 60 and a memory module 70. The biometrically activated device is activated by the contact of a user 80 with the biometric sensor 60 of the device 50. Preferably, the user 80 will activate the device 50 by placing a finger on the biometric sensor 60 for a period of time sufficient for the biometric sensor 60 to perform a scan of at least one unique internal biometric marker of the user 80. It is also understood that the device 50 may be remotely activated or may be maintained in an activated state.

Activation of the device 50 triggers the emission of energy 65 from an emission device 61. The energy 65 is directed towards a user 80 where it is both absorbed and reflected. The portion of energy 65 reflected back at the device 50 is measured by a receiving device 62. The receiving device 62 interprets the amount of energy 65 received and converts the energy into an electrical signal 66 which is communicated to the memory module 70 of the device 50. In alternate embodiments, the energy received by the receiving device 62 is converted to an electrical signal 66 by a translator (not shown).

The memory module 70 receives the electrical signal 66 and begins an authentication process of comparing an internal biometric marker, or markers, of the user 80 with the biometric marker, or markers, of the authorized users stored in the memory module 70. The characteristics of the electrical signal 66 represent the internal biometric marker, or markers, which the biometric sensor 60 obtains from the user 80. The memory module 70 compares the electrical signal 66 to a known biometric profile 76 stored within the memory module 70. If the electrical signal 66 is identical to the known biometric profile 76, the biometrically activated device has authenticated the user 80 and allows access to the data 72 stored within the memory module 70. If the electrical signal 66, is not authenticated, the biometric device 50 denies access to the data 72 stored within the memory module 70. Preferably, when access to the data 72 is denied, the biometric device 50 automatically turns off.

Although the electrical signal 66 may be directly compared to the known biometric profile 76, the electrical signal 66 may also be transformed within the memory module 70 prior to comparison with the known biometric profile 76. The electrical signal 66 may be transformed into a mathematical representation or value based on algorithms programmed into the memory module 70. The algorithms typically represent the necessary transforms needed to interpret the internal biometric marker represented by the electrical signal 66. The mathematical representation or value, which represents the biometric profile of the user 80, is compared to a known biometric profile 76 stored within the memory module 70. If the mathematical representation or value is authenticated, access to the data 72 stored in the memory module is allowed.

Once accessed, the data 72 stored within the biometric device 50 may be displayed in some manner or used to perform an act on another device. For example, the data 72 may be displayed on an output device. Likewise, the data 72 may trigger the execution of a program within the memory module 70 such that the memory module 70 causes the actuation of a device, such as a door lock, in communication with the memory module. Further examples are described herein.

Figure 2:
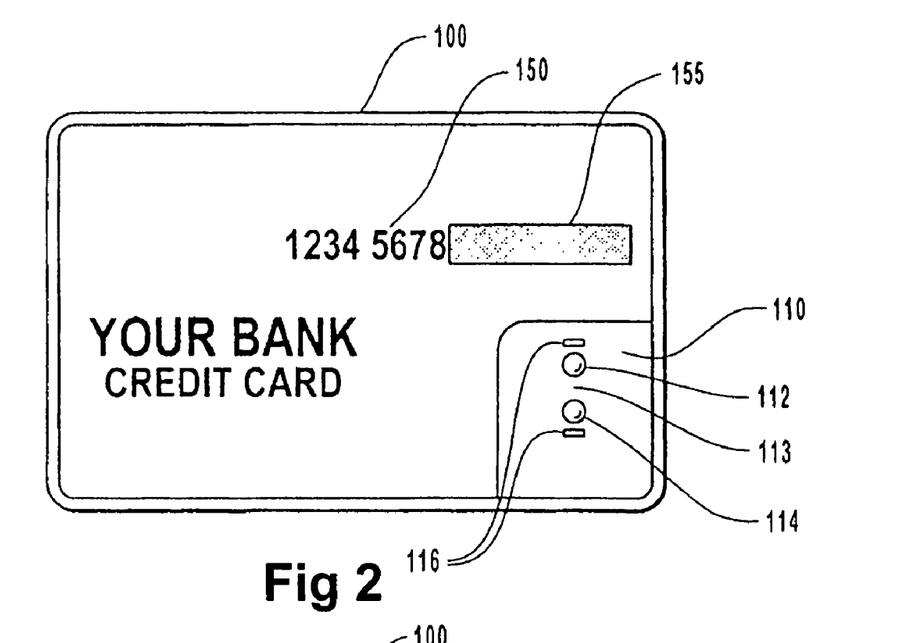
FIG. 2 is a plan view of one embodiment of the biometric device of the present invention.

FIG. 2 illustrates another preferred embodiment of a biometrically activated device: a credit card. A biometrically activated device is an integral portion of a biometric device 100, which in this case has the same shape, size and dimensions as a typical credit card. It is understood, however, that the shape, size, and dimensions of the credit card are not limiting to the invention.

As illustrated, the biometric device 100 includes a biometric sensor having a light emitter 112 and a light acceptor 114. The biometric sensor 110 may additionally include an activation device 116 as shown in FIG. 2. Activation of the biometric sensor 110 triggers the light emitter 112 to emit a light 113. An example of a suitable light emitter 112 is a light emitting diode (LED). Various types of LED's or alternative light sources may be substituted as the light emitter 112 depending upon the desired wavelength and characteristics of light 113 emanating therefrom. The light acceptor 114 can be any device capable of absorbing reflected light 113.

In normal use, an individual wishing to use the biometric device 100 places a body part, such as a thumb or finger, over the biometric sensor 110 such that light 113 emitted from light emitter 112 is directed toward the body part and is reflected back towards the light acceptor 114. Typically, the biometric sensor 110 will include an activation switch 116 which activates the biometric sensor 110 when a body part is placed over the biometric sensor 110, and causes light 113 to be emitted from the light emitter 112 for a fixed duration of time. Light 113 is partially absorbed and partially reflected by the body part covering the biometric sensor 110. Reflected light 113 is monitored by the light acceptor 114.

A preferred embodiment of the invention utilizes an infra red LED, which emits sufficient infra red light to penetrate the epidermal layer of skin of a user. A portion of the infra red light is reflected back to the light acceptor 114 while the remainder of the light is absorbed or lost. Based upon the amount of light reflected back to the light acceptor 114 over a period of time, a biometric profile may be established. The portion of the light signal received by the light acceptor 114 is compared to biometric data or a biometric profile stored within the biometric device 100. If the light signal is identical to the biometric profile stored within the biometric device 100, the biometric device is activated. Where the light signal does not correspond to the stored biometric data or profile, the biometric device is not activated and the biometric sensor 110 is temporarily turned off.

Figure 3:
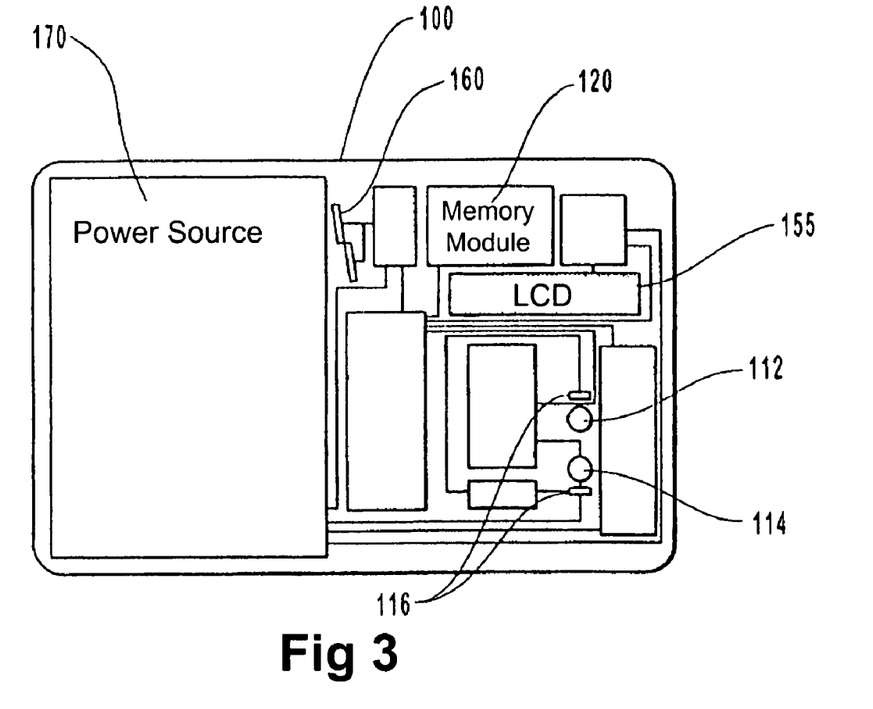
FIG. 3 is a cut-away plan view of the biometric device of FIG. 2.

Activation of the biometric device 100 requires proper identification of the user of the biometric device 100. FIG. 3 depicts a cut-away plan view of the biometric device 100 exposing a memory module 120 in communication with the light acceptor 114 of the biometric sensor 110. The biometric profile of the authorized user is stored within the memory module 120. Other data, such as account codes, names, addresses, pass codes, or graphics, may also be stored within the memory module 120. Once a biometric profile of the user is constructed by the biometric sensor 110, the user's biometric profile is compared to the biometric profile stored within memory module 120. If the user's biometric profile matches that of the biometric profile of the authorized user stored in the memory module 120, the memory module allows access to at least a portion of the additional data or information stored within the memory module 120.

The biometric sensor 110 may also include a translator (not shown) which interprets the level of light or energy received by the light acceptor 114 and constructs a biometric profile based upon the data received. The translator may also be an integral portion of the light acceptor 114 wherein the amount of accepted light is transformed into an electric signal. The biometric profile is then compared to the biometric data or profile stored within the memory module 120.

Figure 4:
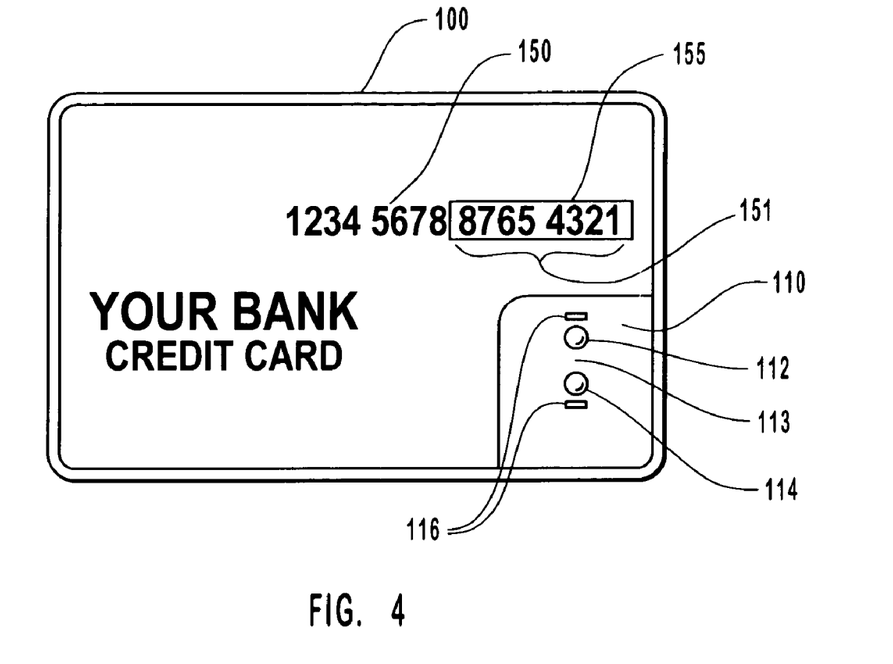
FIG. 4 is a plan view of the biometric device of FIG. 2 in an activated state.
Figure 5:
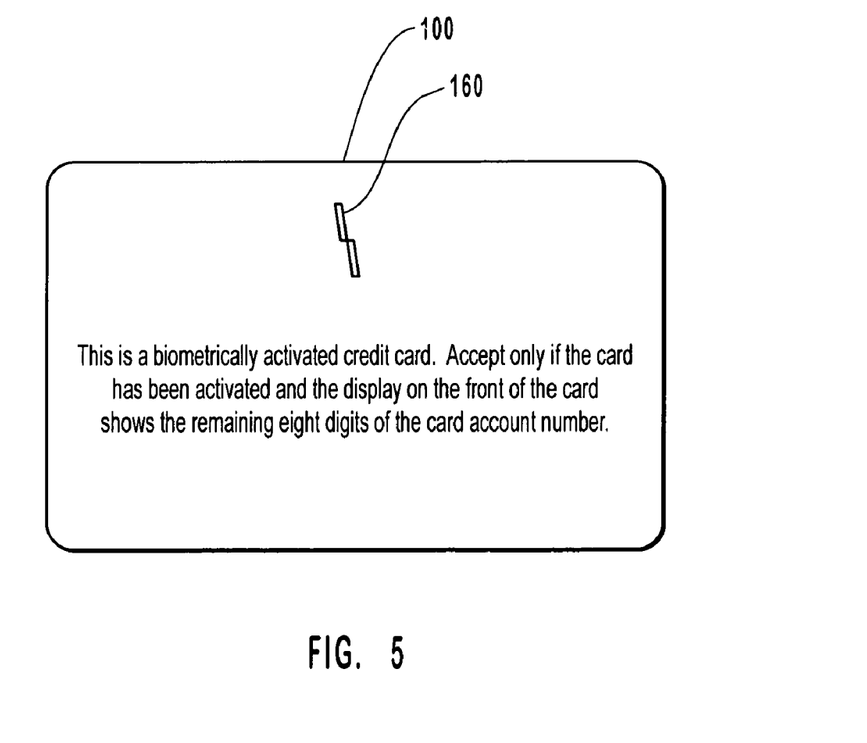
FIG. 5 is a plan view of the back side of the biometric device of FIG. 2.

Upon activation of the biometric device 100 of FIGS. 2 and 3, the memory module 120 releases the information, such as account information, required to perform an electronic transaction. The information stored in the memory module 120 may be released in a number of ways. As illustrated in FIG. 2, only a portion of the account numbers 150 are embossed on the biometric device 100. In the instant example, a blank liquid crystal display (LCD) 155 is positioned next to the account numbers 150. Upon activation of the biometric device 100, the memory module 120 activates the LCD 155 and communicates the information necessary to display the remaining account numbers 151 on the LCD 155, as illustrated in FIG. 4. Likewise, upon activation of the biometric device 100, the memory module 120 may repeatedly send account information to a magnetic transmitter 160 on the biometric device, as depicted in FIG. 5. The magnetic transmitter 160 shown in FIG. 5 may reside in the same location occupied by the magnetic strip of a credit card, such that the biometric device 100 may be used in the same manner as a credit card upon activation.

Other methods or devices for communicating the data or information stored within the memory module 120 may also be used. For example, the LCD 155 could be replaced with LED's or alternative display devices. Likewise, the magnetic transmitter 160 may be replaced with a digital device providing digital signals for a transaction or a light emitter which would release the data or information stored in the memory module 120 by the emission of visible or non-visible light.

It is intended that the biometric device be self-calibrating. For example, the original biometric data or profiles stored in the memory module 120 may be calibrated through repetitive use. As the biometrically activated device is used, the biometric profiles obtained are averaged such that a specific number of the most recent successful biometric readings, offset by the original biometric profile, are used to create a more complete biometric profile of the authorized user.

As part of the built-in security feature, the biometric device 100 can automatically deactivate. For example, the memory module 120 may be programmed such that, once the user is authenticated and the biometric device is activated, the memory module 120 will display the account numbers 150 on an LCD 155 and/or repeatedly send account information to a magnetic transmitter 160 for a fixed duration of time. Thus, access to the information stored within the memory module 120 may be limited to a specific period of time needed to carry out an electronic transaction. This feature advantageously prevents the unnecessary display of account numbers 150 and electronic copying of information permanently stored in magnetic strips of current credit cards. In addition, because the biometric device 100 may only be activated by the authorized user, others are prevented from using the biometric device 100 to perform an invalid transaction.

The biometric device 100 may further include a power source 170 to supply the necessary energy for the operation of the biometric device 100, as depicted in FIG. 3. The power source may be in the form of a battery, a capacitor, a fuel cell, or alternative energy-producing or storage mechanism. Likewise, the power source may be rechargeable. Examples of alternative power sources include photocells, piezo electric generators, static generators, heat absorbers and other power generation mechanisms.

Use of the biometrically activated device of the present invention is not limited to use in credit cards. For example, a security badge could employ the present invention, allowing only the authorized user the ability to use the security badge. Likewise, drivers licenses or other identification cards using the biometrically activated device would guarantee that only the authorized user could properly operate the biometric device. For example, a drivers license could employ a biometrically activated device. The data on a drivers license, or the picture of the individual owning the drivers license, stored within the memory module could be displayed upon the proper authentication of the user of the license.

The biometrically activated device of the instant invention could additionally be utilized in cell phones. As cell phones become more advanced and more information is stored within the cell phone, it is desirable to provide a means with which to secure the data stored therein. As cell phones and Personal Data Assistants (PDA) are integrated and combined, the need for security will become even more imperative. In order to protect such devices and restrict access to the authorized users of the device, a cell phone or PDA (or combination thereof) could be equipped with the biometrically activated device of the present invention. Thus, the cell phone or PDA could only be activated by the owner or other authorized user of the device.

Additional components connected to the biometrically activated device also expand the uses of the device. For example, instead of releasing data, such as account numbers, the memory module 120 of the device could be programmed to actuate a mechanical device, such as a door lock. The necessary control codes, or required programming in the biometrically activated device allow a user to perform mechanical functions based upon the proper authentication of the user.

It is understood that the present invention is not limited in use, but rather may be employed in any environment where it is necessary or desirous to provide an inexpensive and portable security measure which restricts use of a device to individuals having certain, programmed biometric profiles to access data or information stored within the device or initiate a process.

Embodiments of the present invention can include, but are not limited to, card-based products such as credit cards, smart cards, debit cards, ATM access cards, facilities access cards, security cards, identification cards or other card-based products requiring secure use or activation. Also included, for example, are activation mechanisms for products such as computers, microcomputers, PDA's (personal data assistants), cell phones, secure access systems, secure entry systems, software access mechanisms, PIN number replacement, firearm locks, transaction activation, or voting mechanisms. The present invention can additionally be utilized as a security feature in drivers licenses, passports, theme park passes, safebox access and the like. Further examples include the combination of the present invention with an interactive display screen or computer device to protect computers or information transmitted over the internet.

Having thus described certain preferred embodiments of the present invention, it is understood that the invention defined by the appended claims is not to be limited by particular details set forth in the above description, as many apparent variations thereof are possible without departing from the spirit or scope thereof as hereinafter claimed.

What is claimed is:

1. A device activated by biometric authentication, comprising:
   a biometric sensor configured to measure a plurality of different specific, internal, physiological characteristics of a user, said biometric sensor comprising,
      an energy emitter configured to emit an electromagnetic energy signal toward said user, wherein said electromagnetic energy signal is configured to penetrate said user to measure one or more of said specific, internal, sub-epidermal physiological characteristics of said user, and
      an energy sensor configured to detect an electromagnetic energy signal returned from said user responsive to said emitted electromagnetic energy signal to thereby obtain a measurement of said one or more specific, internal, sub-epidermal physiological characteristics of said user; and
   a memory module in communication with said biometric sensor comprising a biometric profile of an authorized user of said device,
   wherein the device is configured to select a first one and a second one of said plurality of specific, internal, sub-epidermal physiological characteristics of said user, emit an electromagnetic energy signal from said electromagnetic energy emitter to measure said first specific, internal, sub-epidermal physiological characteristic, and said second specific, internal, sub-epidermal physiological characteristic, receive a returned energy signal comprising said measurements of said first and second specific, internal, sub-epidermal physiological characteristics of said user, determine a first biometric marker of said user using said measurement of said first specific, internal, sub-epidermal physiological characteristic, determine a second biometric marker of said user using said measurement of said second specific, internal sub-epidermal physiological characteristic, and generate an authentication signal if said first biometric marker and said second biometric marker match a biometric profile of an authorized user of said device.

2. A device activated by biometric authentication, comprising:
   a biometric sensor configured to measure a plurality of different specific, internal, physiological characteristics of a user, said biometric sensor comprising,
      an energy emitter configured to emit an electromagnetic energy signal toward said user, wherein said electromagnetic energy signal is configured to penetrate said user to obtain measurements of one or more of said plurality of specific, internal, sub-epidermal physiological characteristics of said user, and an energy sensor configured to detect an electromagnetic energy signal returned from said user responsive to said emitted electromagnetic energy signal to thereby obtain measurements of said one or more specific, internal, sub-epidermal physiological characteristics of said user; and a memory module in communication with said biometric sensor comprising a biometric profile of an authorized user of said device, wherein the device is configured to select a first one and a second one of said plurality of specific, internal, sub-epidermal physiological characteristics of said user, emit a first electromagnetic energy signal from said electromagnetic energy emitter to measure said first specific, internal, sub-epidermal physiological characteristic, receive a first returned energy signal comprising said measurement of said first specific, internal, sub-epidermal physiological characteristic of said user using said energy sensor, emit a second electromagnetic energy signal from said electromagnetic energy emitter to measure said second specific, internal, sub-epidermal physiological characteristic, receive a second returned energy signal comprising said measurement of said second specific, internal, sub-epidermal physiological characteristic of said user using said energy sensor, determine a first biometric marker of said user using said measurement of said first specific, internal, sub-epidermal physiological characteristic and a second biometric marker of said user using said measurement of said second specific, internal, sub-epidermal physiological characteristic, generate an authentication signal if said first biometric marker and said second biometric marker match a biometric profile of an authorized user of said device.

3. A device activated by biometric authentication, comprising:

a biometric sensor configured to measure a plurality of different specific, internal, sub-epidermal physiological characteristics of a user, the biometric sensor comprising, an energy emitter configured to emit an electromagnetic energy signal toward the user, and an energy sensor configured to detect an electromagnetic energy signal responsive to the emitted electromagnetic energy signal to thereby obtain a measurement of a specific, internal, sub-epidermal physiological characteristic of the user; and a memory module communicatively coupled to the biometric sensor, the memory module comprising a biometric profile of an authorized user of the device, wherein the device is configured to acquire measurements of two or more of the plurality of different specific, internal, sub-epidermal physiological characteristics of the user using the biometric sensor, to determine two or more biometric markers using the two or more measurements, and to generate an authentication signal when the two or more biometric markers match the biometric profile of the authorized user.

4. The device of claim 3, wherein the biometric sensor is configured to prevent identification by a user of the device of the plurality of the specific, internal, sub-epidermal physiological characteristics measured by the biometric sensor.

5. The device of claim 3, wherein a first one of the two or more biometric markers is substantially unique to the user.

6. The device of claim 5, wherein a second one of the two or more biometric markers is substantially unique to the user.

7. The device of claim 3, wherein the device is configured to determine whether the two or more measurements were obtained from a live human using the first one of the two or more biometric markers.

8. The device of claim 7, wherein the device is configured to assert the authentication signal when the first biometric marker indicates that the two or more measurements were obtained from a live human.

9. The device of claim 7, wherein the device is configured to prevent assertion of the authentication signal when the first biometric marker indicates that the two or more measurements were not obtained from a live human.

10. The device of claim 3, wherein a first one of the two or more measurements comprises a heartbeat waveform.

11. The device of claim 3, wherein a first one of the two or more measurements comprises a capillary pattern.

12. The device of claim 3, wherein a first one of the two or more measurements comprises a blood oxygen level.

13. The device of claim 3, wherein the energy emitter comprises a light emitting diode.

14. The device of claim 3, wherein the energy emitter is configured to emit optical energy in the infra-red spectrum.

15. The device of claim 3, wherein the energy emitter is configured to emit optical energy at one of a plurality of different wavelengths.

16. The device of claim 3, wherein the device comprises a cell phone.

17. The device of claim 3, wherein the device comprises a portable computing device.

18. The device of claim 3, wherein the device comprises a communications device capable of communication with a communications network.

19. The device of claim 3, wherein activating the device comprises causing the device to transmit at least one of the two or more measurements and at least one of the two or more biometric markers on the communications network.

20. The device of claim 3, wherein a first one of the two or more measurements comprises one of a cardiac rhythm, a capillary density, a blood oxygen level, sub-dermal layer analysis, a diacrotic notch, and a hematocrit level.

21. A method for authenticating a user of a device comprising a biometric sensor, the method comprising:

acquiring two or more measurements of different specific internal, sub-epidermal physiological characteristics of an individual using the biometric sensor, the biometric sensor comprising an optical energy emitter and an optical energy sensor, wherein acquiring a measurement comprises, emitting an optical energy signal toward the individual using the optical energy emitter, and sensing an optical energy signal responsive to the emitted optical energy signal using the optical energy sensor, and determining a measurement of an internal, sub-epidermal physiological characteristic of the individual using the sensed optical energy signal;

deriving two or more biometric markers from the two or more measurements acquired using the biometric sensor;

comparing the two or more biometric markers to a biometric profile of an authorized user of the device; and asserting an authentication signal when the two or more biometric markers match the biometric profile of the authorized user.

22. The method of claim 21, wherein the biometric sensor is configured to prevent identification of the specific, internal, sub-epidermal physiological, characteristics measured by the biometric sensor.

23. The method of claim 21, wherein a first one of the two or more biometric markers is substantially unique to the individual.

24. The method of claim 23, wherein a second one of the two or more biometric markers is substantially unique to the individual.

25. The method of claim 21, further comprising determining whether the two or more measurements were acquired from a live human using a first one of the two or more biometric markers.

26. The method of claim 25, wherein the authentication signal is asserted when the first one of the two or more biometric markers determines that the two or more measurements were acquired from a live human.

27. The method of claim 26, further comprising preventing assertion of the authentication signal when the first one of the two or more biometric markers determines that the two or more measurements were not acquired from a live human.

28. The method of claim 21, wherein a first and a second one of the two or more measurements are obtained by emitting a single optical energy signal towards the individual using the optical energy emitter of the biometric sensor.

29. The method of claim 21, wherein the optical energy emitter comprises a light emitting diode.

30. The method of claim 21, wherein the optical energy emitter is configured to emit optical energy in the infra-red spectrum.

31. The method of claim 21, wherein the optical energy emitter is configured to emit optical energy at one of a plurality of different wavelengths.

32. The method of claim 21, wherein a first one of the two or more measurements comprises one of a cardiac rhythm, a capillary density, a blood oxygen level, sub-dermal layer analysis, a diacrotic notch, and a hematocrit level.

33. The method of claim 21, wherein the device comprises a communications device capable of communication on a network.

34. The method of claim 33, wherein the device comprises one of a mobile phone, a portable computing device, and a personal digital assistant.

35. The method of claim 34, further comprising activating the device responsive to deriving the two or more biometric markers, wherein activating the device comprises using the device to transmit one or more of the measurements and one or more of the biometric markers using the device.

* * * * *

UNITED STATES PATENT AND TRADEMARK OFFICE
CERTIFICATE OF CORRECTION

| | | |
|---|---|---|
| PATENT NO. | : 7,796,013 B2 | Page 1 of 1 |
| APPLICATION NO. | : 09/758836 | |
| DATED | : September 14, 2010 | |
| INVENTOR(S) | : Murakami et al. | |

It is certified that error appears in the above-identified patent and that said Letters Patent is hereby corrected as shown below:

Column 1, Line 24 reads, "...from harms way..." which should read, "...from harm's way..."

Column 1, Line 47 reads, "...wherein a persons 'identity' is stolen." which should read, "...wherein a person's 'identity' is stolen."

Column 2, Line 53 reads, "...byway of fingerprint." which should read, "...by way of fingerprint."

Column 3, Line 4 reads, "...which scan a external..." which should read, "...which scan an external..."

Column 3, Line 10 reads, "...and 5,335,288 Internal..." which should read, "...and 5,335,288. Internal..."

Column 3, Line 13 reads, "...verifying physiological process, such as..." which should read, "...verifying a physiological process, such as..."

Column 3, Line 17 reads, "...such biometric readings are describe..." which should read, "...such biometric readings are described..."

Column 4, Line 60 reads, "...biometric markers, however..." which should read, "...biometric markers; however..."

Column 11, Line 30 reads, "...generate an authentication signal..." which should read, "...and generate an authentication signal..."

Signed and Sealed this
Twenty-eighth Day of December, 2010

David J. Kappos
*Director of the United States Patent and Trademark Office*